United States Patent
Kato et al.

(10) Patent No.: US 11,141,074 B2
(45) Date of Patent: Oct. 12, 2021

(54) PULSE WAVE DETECTOR, BIOLOGICAL INFORMATION MEASUREMENT DEVICE, PULSE WAVE DETECTION METHOD AND STORAGE MEDIUM

(71) Applicant: OMRON HEALTHCARE CO., LTD., Kyoto (JP)

(72) Inventors: Yuki Kato, Muko (JP); Shingo Yamashita, Muko (JP); Toshihiko Ogura, Muko (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 403 days.

(21) Appl. No.: 16/161,660

(22) Filed: Oct. 16, 2018

(65) Prior Publication Data
US 2019/0046050 A1   Feb. 14, 2019

Related U.S. Application Data

(63) Continuation of application No. PCT/JP2017/015751, filed on Apr. 19, 2017.

(30) Foreign Application Priority Data

Apr. 27, 2016   (JP) .............. JP2016-089791

(51) Int. Cl.
*A61B 5/0225* (2006.01)
*A61B 5/022* (2006.01)
(Continued)

(52) U.S. Cl.
CPC .............. *A61B 5/0225* (2013.01); *A61B 5/02* (2013.01); *A61B 5/022* (2013.01);
(Continued)

(58) Field of Classification Search
CPC ......... A61B 5/0225; A61B 5/022; A61B 5/02; A61B 5/02108; A61B 5/6843;
(Continued)

(56) References Cited

U.S. PATENT DOCUMENTS 4,269,193 A   5/1981  Eckerle
6,321,601 B1  11/2001 Maris
(Continued)

FOREIGN PATENT DOCUMENTS

CN   1980602      6/2007
CN   101589860   12/2009
(Continued)

OTHER PUBLICATIONS

Office Action dated Oct. 21, 2020 in corresponding Chinese Patent Application No. 201780026138.0 with English-language translation.
(Continued)

*Primary Examiner* — Sean P Dougherty
*Assistant Examiner* — Kyle W. Kretzer
(74) *Attorney, Agent, or Firm* — Wenderoth, Lind & Ponack, L.L.P.

(57) ABSTRACT

A pulse wave detection method includes: increasing a pressing force of a pressing member for pressing a strain sensor fixed thereto against a body surface, the flexible strain sensor having a plurality of strain detection elements arranged on a substrate; determining a deformation stop timing at which deformation of a detection face of the strain sensor has been stopped based on the strain detection signal detected by each of the plurality of strain detection elements in a pressure raising process in which the pressing force is increased; setting a level of the strain detection signal detected at the deformation stop timing as a reference level; calibrating the first strain detection signal detected after the deformation
(Continued)

stop timing based on the reference level; and generating a pressure signal from the calibrated first strain detection signal.

8 Claims, 6 Drawing Sheets

(51) Int. Cl.
    *A61B 5/02*         (2006.01)
    *A61B 5/021*       (2006.01)
    *A61B 5/00*         (2006.01)
    *G01L 27/00*       (2006.01)

(52) U.S. Cl.
    CPC ........ *A61B 5/02108* (2013.01); *A61B 5/6843* (2013.01); *A61B 5/6824* (2013.01); *G01L 27/00* (2013.01); *G01L 27/002* (2013.01); *G01L 27/005* (2013.01)

(58) Field of Classification Search
    CPC ..... A61B 5/6824; A61B 5/021; A61B 5/0205; G01L 27/00; G01L 27/002; G01L 27/005
    See application file for complete search history.

(56) References Cited

U.S. PATENT DOCUMENTS

| | | | |
|---|---|---|---|
| 6,533,729 B1* | 3/2003 | Khair | A61B 5/021 600/480 |
| 9,689,770 B2* | 6/2017 | Hammerschmidt | G01L 9/0073 |
| 10,736,520 B2* | 8/2020 | Kitagawa | A61B 5/742 |
| 2001/0003792 A1* | 6/2001 | Ogura | A61B 5/02125 600/500 |
| 2004/0210142 A1 | 10/2004 | Satoh et al. | |
| 2005/0038347 A1 | 2/2005 | Suzuki et al. | |
| 2006/0206031 A1 | 9/2006 | Hasegawa | |
| 2008/0097250 A1 | 4/2008 | Tochigi et al. | |
| 2011/0295128 A1 | 12/2011 | Yuasa et al. | |
| 2014/0228693 A1 | 8/2014 | Yuasa et al. | |
| 2014/0236028 A1 | 8/2014 | Yuasa et al. | |
| 2015/0164348 A1 | 6/2015 | Yuasa et al. | |
| 2017/0238820 A1 | 8/2017 | Yuasa et al. | |

FOREIGN PATENT DOCUMENTS

| | | |
|---|---|---|
| CN | 202051696 | 11/2011 |
| CN | 104398246 | 3/2015 |
| CN | 204575226 | 8/2015 |
| EP | 0 152 848 | 8/1985 |
| EP | 0 333 442 | 9/1989 |
| JP | 2002-148132 | 5/2002 |
| JP | 2004-208711 | 7/2004 |
| JP | 2004-313409 | 11/2004 |
| JP | 2006-226751 | 8/2006 |
| JP | 2006-280485 | 10/2006 |
| JP | 2011-244938 | 12/2011 |
| JP | 3174783 | 4/2012 |
| WO | 01/85024 | 11/2001 |

OTHER PUBLICATIONS

International Search Report dated Jul. 18, 2017 in International (PCT) Application No. PCT/JP2017/015751.
Written Opinion of the International Search Authority dated Jul. 18, 2017 in International (PCT) Application No. PCT/JP2017/015751.
Extended European Search Report dated Nov. 5, 2019 in corresponding European Patent Application No. 17789377.3.

\* cited by examiner

PULSE WAVE DETECTOR, BIOLOGICAL INFORMATION MEASUREMENT DEVICE, PULSE WAVE DETECTION METHOD AND STORAGE MEDIUM

CROSS-REFERENCE TO RELATED APPLICATIONS

This is a Continuation of International Patent Application No. PCT/JP2017/015751 filed Apr. 19, 2017, which claims the benefit of Japanese Patent Application No. 2016-089791 filed Apr. 27, 2016. The disclosures of the prior applications are hereby incorporated by reference herein in their entireties.

TECHNICAL FIELD

Aspects of the present invention relate to a pulse wave detector, a biological information measurement device, a pulse wave detection method and a storage medium.

BACKGROUND ART

A biological information measurement device is known that, in a state where a sensor is made contact with the body surface of a living body portion through which an artery such as the radial artery in the wrist passes, can measure biological information such as the pulse, heartbeat or blood pressure by using information detected by this sensor (see Patent Literature 1 (JP-A-2011-244938), Patent Literature 2 (JP-A-2004-208711), and Patent Literature 3 (JP-A-2002-148132)).

Patent Literature 1 describes a blood pressure sensor having a plurality of magnetoresistance effect elements disposed in a two-dimensional form on a flexible substrate to detect strains as resistance values and a pressing mechanism for pressing the flexible substrate against the body surface.

Patent Literature 1 discloses, as a method for measuring blood pressure using this blood pressure sensor, a method for converting the resistance values detected by the magnetoresistance effect elements into a blood pressure value using the correlation data between the blood pressure obtained by actual measurement beforehand and the resistance values of the magnetoresistance effect elements.

Patent Literature 2 describes a pulse wave detection sensor having a flexible sheet on which strip-shaped flexible sheets are disposed so as to intersect therewith and an elastic member fixed to the rear face of the flexible sheet.

Patent Literature 3 describes a device for measuring biological information such as blood pressure using a sensor having a plurality of magnetoresistance effect elements disposed in a two-dimensional form on a flexible substrate.

As described in Patent Literatures 1 to 3, with a configuration in which biological information is measured by making the sensor having flexibility contact with the body surface, the feeling of wearing the sensor can be made excellent.

Furthermore, since information required for the calculation of the biological information can be detected using more elements, the calculation accuracy of the biological information can be improved.

As a method for detecting a pulse wave serving as a piece of information to be used for the calculation of biological information, a tonometry method is generally known. The tonometry method is a method for detecting a pressure pulse wave (a pressure oscillating wave transmitted to the body surface due to pulsation) from an artery using a sensor in the state (tonometry state) in which the artery is pressed and flattened appropriately.

Hence, the method requires a pressing mechanism for pressing the sensor against the body surface and a drive section for driving this pressing mechanism.

Patent Literature 1 describes a biological information measurement device equipped with a blood pressure sensor, a pressing mechanism for pressing the blood pressure sensor against the body surface and a drive section for driving this pressing mechanism. The blood pressure sensor detects the tensile stress occurring in the sensor due to pulsation as a resistance value using the magnetoresistance effect elements and converts this resistance value into blood pressure.

Furthermore, because the blood pressure sensor described in Patent Literature 1 has flexibility, in the state in which the blood pressure sensor is pressed against the body surface, the magnitude of the strain applied to each of the plurality of magnetoresistance effect elements becomes different depending on the position of the magnetoresistance effect element. Hence, a pressure pulse wave cannot be detected accurately if the difference in the strain is not taken into consideration.

In Patent Literature 2, the flexible sheet is not supposed to be pressed against the body surface, and a method for detecting a pressure pulse wave in the state in which the flexible sheet is pressed against the body surface is not taken into consideration.

In Patent Literature 3, the flexible substrate is not supposed to be pressed against the body surface, and a method for detecting a pressure pulse wave in the state in which the flexible substrate is pressed against the body surface is not taken into consideration.

Therefore, there is no technique to provide a pulse wave detector capable of accurately detecting a pressure pulse wave in the state in which a flexible sensor is pressed against a body surface, a biological information measurement device, a method for controlling the pulse wave detector, and a program for controlling the pulse wave detector.

SUMMARY

A pulse wave detector related to one aspect of the present invention includes: a flexible strain sensor having a plurality of strain detection elements arranged on a substrate; a flexible pressing member for pressing the strain sensor fixed thereto against a body surface of a living body; a drive section for driving the pressing member; a pressing control section for controlling a pressing force of the pressing member for pressing the strain sensor against the body surface by controlling the drive section; a deformation stop timing determination section for determining a deformation stop timing at which deformation of a detection face of the strain sensor has been stopped based on a strain detection signal detected by each of the plurality of strain detection elements in a pressure raising process in which the pressing force is increased by the pressing control section; a calibration section for setting a level of the strain detection signal detected by each of the plurality of strain detection elements at the deformation stop timing as a reference level and for calibrating a first strain detection signal detected by each of the plurality of strain detection elements after the deformation stop timing based on the reference level; and a pressure generation section for generating a pressure signal from the calibrated first strain detection signal.

A biological information measurement device related to one aspect of the present invention includes: a pulse wave detector; and a biological information calculation section for calculating biological information based on the pressure signal generated by the pulse wave detector. And the pulse wave detector includes: a flexible strain sensor having a plurality of strain detection elements arranged on a substrate; a flexible pressing member for pressing the strain sensor fixed thereto against a body surface of a living body; a drive section for driving the pressing member; a pressing control section for controlling a pressing force of the pressing member for pressing the strain sensor against the body surface by controlling the drive section; a deformation stop timing determination section for determining a deformation stop timing at which deformation of a detection face of the strain sensor has been stopped based on a strain detection signal detected by each of the plurality of strain detection elements in a pressure raising process in which the pressing force is increased by the pressing control section; a calibration section for setting a level of the strain detection signal detected by each of the plurality of strain detection elements at the deformation stop timing as a reference level and for calibrating a first strain detection signal detected by each of the plurality of strain detection elements after the deformation stop timing based on the reference level; and a pressure generation section for generating the pressure signal from the calibrated first strain detection signal.

A pulse wave detection method related to one aspect of the present invention includes: increasing a pressing force of a pressing member for pressing a strain sensor fixed thereto against a body surface, the flexible strain sensor having a plurality of strain detection elements arranged on a substrate; determining a deformation stop timing at which deformation of a detection face of the strain sensor has been stopped based on the strain detection signal detected by each of the plurality of strain detection elements in a pressure raising process in which the pressing force is increased; setting a level of the strain detection signal detected by each of the plurality of strain detection elements at the deformation stop timing as a reference level; calibrating the first strain detection signal detected by each of the plurality of strain detection elements after the deformation stop timing based on the reference level; and generating a pressure signal from the calibrated first strain detection signal.

A computer-readable non-transitory storage medium that relates to one aspect of the present invention and stores a program for causing a computer to execute a process includes: increasing a pressing force of a pressing member for pressing a strain sensor fixed thereto against a body surface, the flexible strain sensor having a plurality of strain detection elements arranged on a substrate; determining a deformation stop timing at which deformation of a detection face of the strain sensor has been stopped based on the strain detection signal detected by each of the plurality of strain detection elements in a pressure raising process in which the pressing force is increased; setting a level of the strain detection signal detected by each of the plurality of strain detection elements at the deformation stop timing as a reference level; calibrating the first strain detection signal detected by each of the plurality of strain detection elements after the deformation stop timing based on the reference level; and generating a pressure signal from the calibrated first strain detection signal.

DESCRIPTION OF EMBODIMENTS

An embodiment of the present invention will be described below referring to the drawings.

Figure 1:
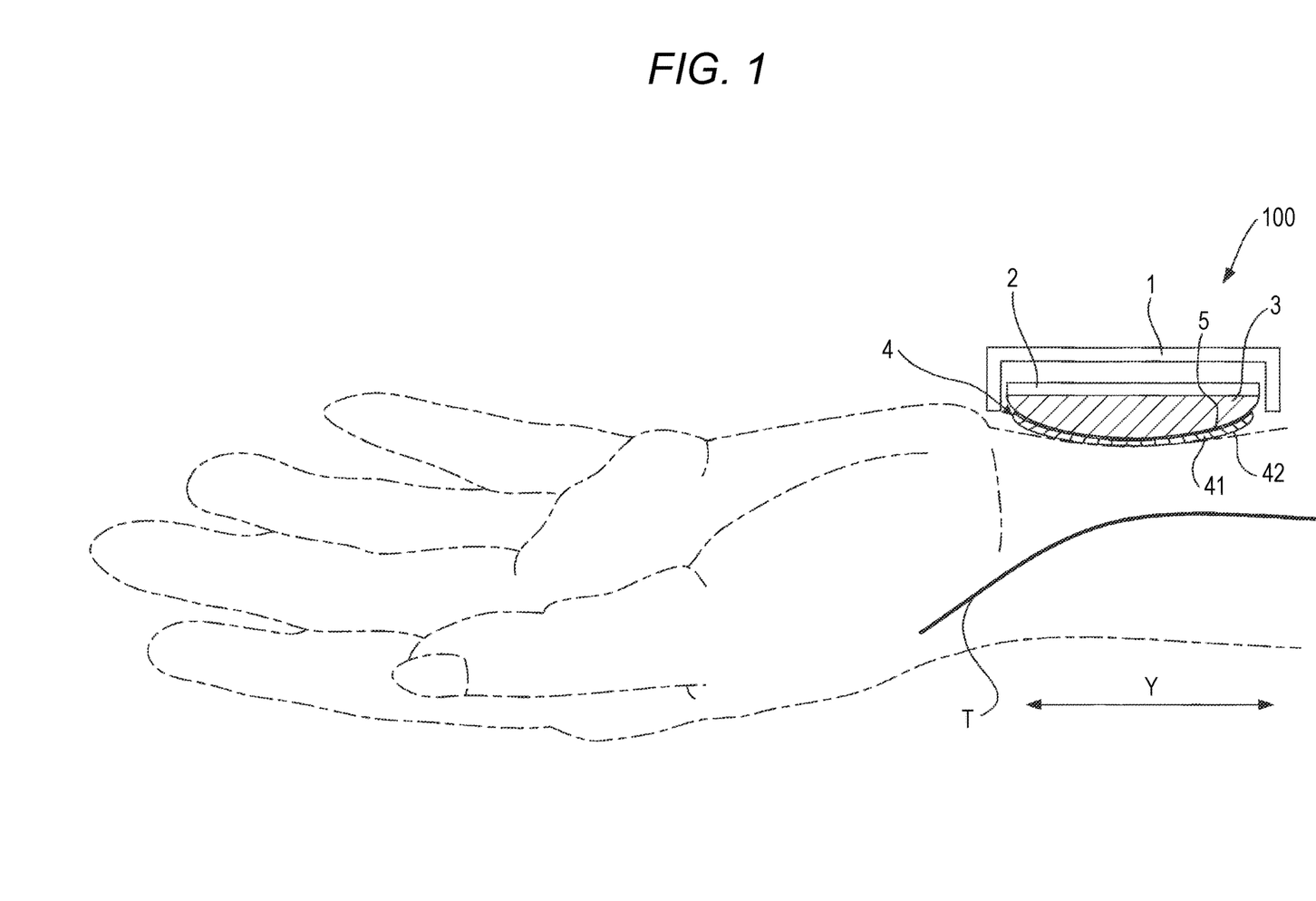
FIG. 1 is a schematic view showing the external configuration of the pulse wave detecting section 100 included in a biological information measurement device according to an embodiment of the present invention.

FIG. 1 is a schematic view showing the external configuration of the pulse wave detecting section 100 included in a biological information measurement device according to the embodiment. The biological information measurement device according to this embodiment is attached by a band, not shown, to a living body portion (the wrist of the left hand of the user in the example shown in FIG. 1) in which an artery (the radial artery T in the example shown in FIG. 1) to be measured to obtain biological information exists therein, and the measurement device is used.

The pulse wave detecting section 100 is equipped with a strain sensor 4, an air bag 3, an adhesive layer 5 for fixing the air bag 3 and the strain sensor 4, a flat plate-shaped supporting member 2 for supporting the air bag 3, and a housing 1 for holding the supporting member 2, the air bag 3 and the strain sensor 4.

The air bag 3 has a hemispherical shape in the example shown in FIG. 1, and the amount of the air (internal pressure) inside the air bag 3 is controlled by a pump, not shown. The air bag 3 is a flexible member, the outer shape of which is deformed as the internal pressure changes. The shape of the air bag 3 is not limited to the hemispherical shape.

In the state in which the pulse wave detecting section 100 is fixed to the wrist as shown in FIG. 1, the air bag 3 functions as a pressing member that presses the detection face 42 of the strain sensor 4 against the body surface of the living body portion (wrist).

Figure 2:
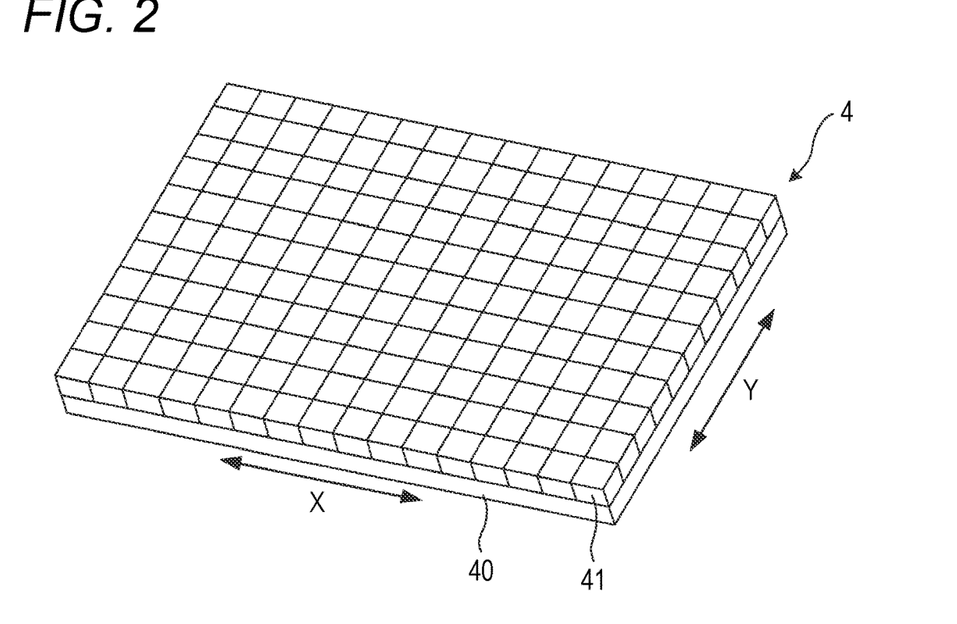
FIG. 2 is a schematic view showing the general configuration of the strain sensor 4 shown in FIG. 1.

FIG. 2 is a schematic view showing the general configuration of the strain sensor 4 shown in FIG. 1.

The strain sensor 4 is equipped with a substrate 40 having flexibility and a plurality of strain detection elements 41 arranged on the surface of the substrate 40. The surface of the substrate 40 is flat. In the example shown in FIG. 2, a plurality of element rows, each including the plurality of strain detection elements 41 arranged in the X-direction, is arranged in the Y-direction orthogonal to the X-direction (the plurality of detection elements 41 is arranged in a two-dimensional form). In the strain sensor 4, at least one of the element rows may merely be formed on the substrate 40.

The strain detection element 41 is an element for detecting the strain generated on the surface of the substrate 40 in an arbitrary direction, and for example a strain gauge that detects strain by sensing the change in the resistance of a metal or a semiconductor or an element that detects strain by using such a magnetoresistance effect as described in Patent Literature 1 is used as the detection element.

The face formed by combining the respective surfaces of the plurality of strain detection elements 41 constitutes the detection face 42 of the strain sensor 4.

The face of the substrate 40 on the opposite side of the surface on which the strain detection elements 41 are formed is fixed to the air bag 3 by the adhesive layer 5 formed of an adhesive member, such as an adhesive or an adhesive tape. Hence, when the air bag 3 is deformed, the strain sensor 4 is also deformed.

In the biological information measurement device according to the embodiment, the detection face 42 of the strain sensor 4 is pressed against the body surface in the state in which the Y-direction shown in FIG. 2 is aligned along the radial artery T to be measured to obtain biological information, and the measurement device is used.

In the attached state shown in FIG. 1, part of the detection face 42 of the strain sensor 4 included in the pulse wave detecting section 100 makes contact with the skin of the wrist of the user. In this state, when the amount of the air to be injected into the air bag 3 increases, the air bag 3 is inflated and the shape thereof is changed, and the strain sensor 4 is pressed against the body surface while being deformed in accordance with the change in the shape of the air bag 3. The internal pressure of the air bag 3 serves as a pressing force when the air bag 3 presses the strain sensor 4 against the body surface.

Figure 3:
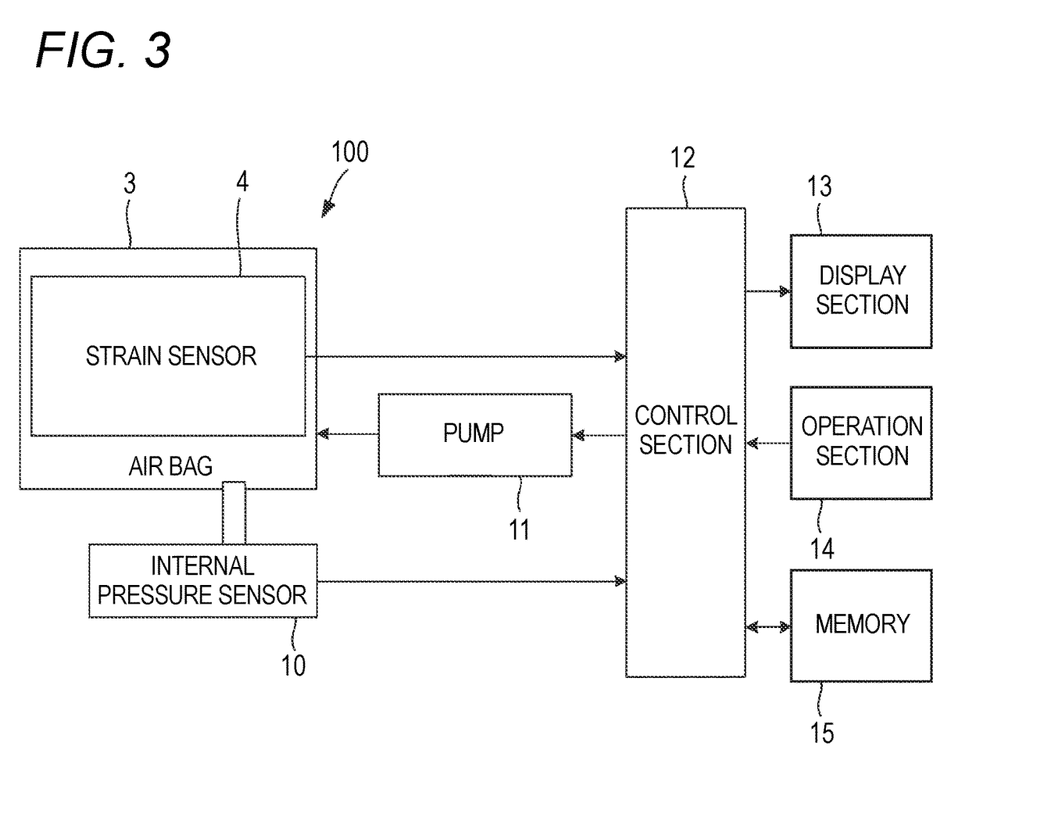
FIG. 3 is a view showing the block configuration of the biological information measurement device according to this embodiment.

FIG. 3 is a view showing the block configuration of the biological information measurement device according to the embodiment.

The biological information measurement device is equipped with the pulse wave detecting section 100, an internal pressure sensor 10, a pump 11, a control section 12 for comprehensively controlling the entire device, a display section 13, an operation section 14, and a memory 15.

The pump 11 controls the amount (the internal pressure of the air bag 3) of the air to be injected into the air bag 3 under the instructions of the control section 12. The pump 11 constitutes a drive section for driving the air bag 3.

The internal pressure sensor 10 detects the internal pressure of the air bag 3 and inputs the detected internal pressure to the control section 12.

The display section 13 is used to display various kinds of information, such as biological information, and is composed of, for example, a liquid crystal display device.

The operation section 14 is an interface for inputting instruction signals to the control section 12 and is composed of, for example, buttons for instructing the start of various operations including the measurement of biological information.

The memory 15 is used to store various kinds of information including the biological information calculated by the control section 12 and is composed of, for example, a flash memory. The memory 15 may be detachable.

The control section 12 is mainly composed of a processor and includes, for example, a ROM (Read Only Memory) in which programs to be executed by the processor, for example, are stored, a RAM (Random Access Memory) serving as a work memory, etc.

These programs include a pulse wave detection program. The ROM is a non-transitory storage medium and the programs stored therein are computer-readable. The programs stored in the ROM may be downloaded from another device and stored.

The output signal of each strain detection element 41 of the strain sensor 4 in the state in which the detection face 42 of the strain sensor 4 is flat is stored in the ROM of the control section 12 as the reference value (hereafter referred to as the strain reference value) of each strain detection elements 41. At the time of manufacturing the biological information measurement device, before the strain sensor 4 is fixed to the air bag 3, the strain reference value is actually measured by the strain sensor 4 and stored in the ROM.

The control section 12 calibrates the output signal of each strain detection element 41 of the strain sensor 4 on the basis of the strain reference value of each strain detection element 41 (performs conversion into a relative value with respect to the strain reference value) and treats the calibrated output signal as the strain detection signal detected by each strain detection element 41.

The processor executes the programs including the pulse wave detection program, whereby the control section 12 functions as a pressing control section, a deformation stop timing determination section, a calibration section, a pressure generation section, and a biological information calculation section.

The pulse wave detecting section 100, the pump 11 and the control section 12 constitutes a pulse wave detector.

The operation of the biological information measurement device according to the embodiment will be described below. The biological information measurement device according to the embodiment has a continuous measurement mode in which the device detects a pressure pulse wave for each beat, calculates biological information on the basis of this pressure pulse wave and stores the biological information.

Figure 4:
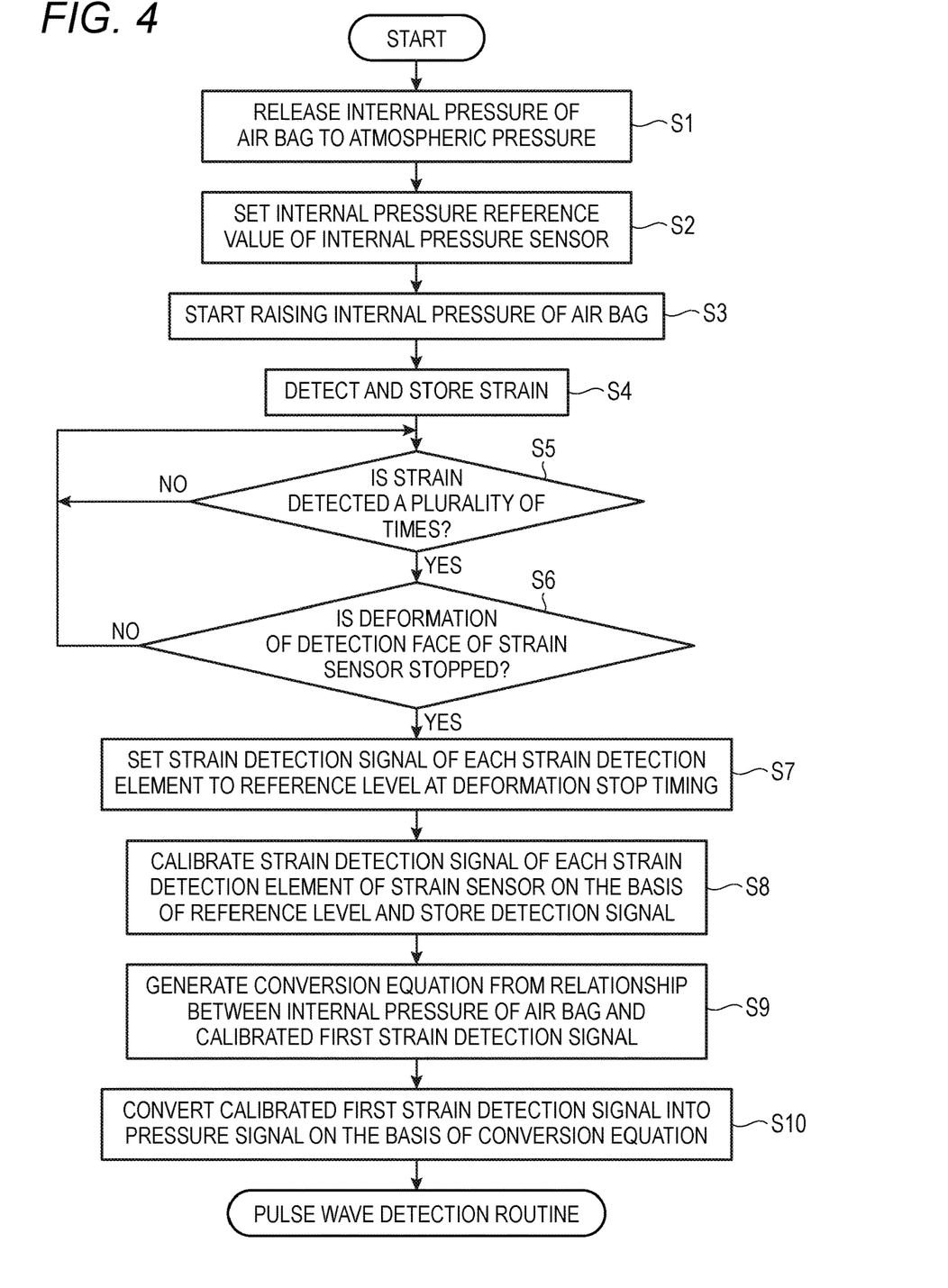
FIG. 4 is a flow chart illustrating the operation in the continuous measurement mode of the biological information measurement device according to the embodiment.

FIG. 4 is a flow chart illustrating the operation in the continuous measurement mode of the biological information measurement device according to the embodiment.

When the biological information measurement device is attached to the wrist and the start of the measurement of biological information is instructed, the control section 12 controls the pump 11 to release the internal pressure of the air bag 3 so that the internal pressure becomes equal to the atmospheric pressure (at step S1).

After step S1, the control section 12 acquires the detection signal of the internal pressure sensor 10 and sets the acquired detection signal as the reference value (internal pressure reference value) of the internal pressure of the air bag 3 (at step S2). Hence, the internal pressure of the air bag 3 detected by the internal pressure sensor 10 is processed as a relative value with respect to this internal pressure reference value.

Figure 5:
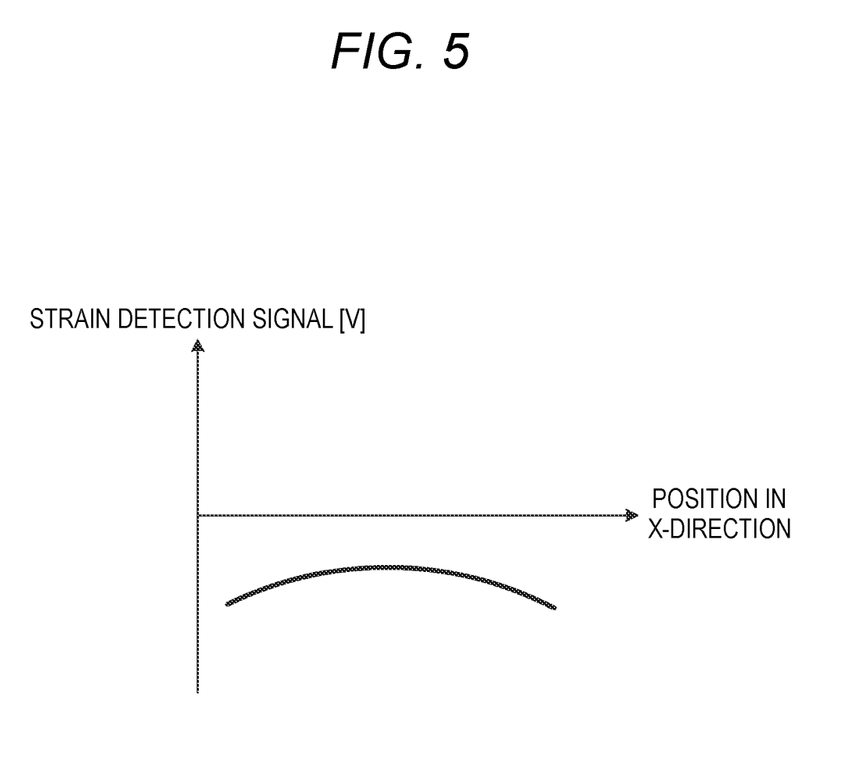
FIG. 5 is a view showing an example of the strain detection signal detected by an arbitrary element row included in the strain sensor 4 in the state in which the process of step S1 in FIG. 4 has been performed.

FIG. 5 is a view showing an example of the strain detection signal detected by an arbitrary element row included in the strain sensor 4 in the state in which the process of step S1 in FIG. 4 has been performed. The horizontal axis in FIG. 5 represents the position of each strain detection element 41 constituting the element row in the X-direction, and the vertical axis in FIG. 5 represents the strain detection signal detected by each strain detection element 41.

The detection signal shown in FIG. 5 has a value calibrated on the basis of the above-mentioned strain reference value stored in the ROM of the control section 12.

The sign of the strain detection signal detected by each strain detection element 41 in the state in which the detection face 42 of the strain sensor 4 is herein bent to the opposite side of the substrate 40 is assumed to be plus. In the state in which the process of step S1 has been performed, the detection face 42 is bent to the side of the substrate 40 along the surface shape of the air bag 3 as shown in FIG. 1. Hence, as shown in FIG. 5, the sign of the strain detection signal is minus. Furthermore, since the strain sensor 4 has flexibility, the detection face 42 has different bending degrees depending on the position. Consequently, as shown in FIG. 5, from each strain detection element 41, the output corresponding to the bending degree of the element at the position where the element is disposed is obtained.

After step S2, the control section 12 controls the pump 11 and starts a pressure raising process for gradually increasing the internal pressure of the air bag 3 (at step S3). The control section 12 stores the information on the internal pressure of the air bag 3 in the memory 15 in association with time.

After the start of the pressure raising process, when strain is detected by each strain detection element 41 of the strain sensor 4, the control section 12 temporarily stores the strain detection signals (strain detection signal groups) detected by each detection element 41 of the strain sensor 4 in the RAM in association with the detection time (at step S4).

After step S4, the control section 12 determines whether a plurality of strain detection signal groups has been stored in the RAM; if stored (YES at step S5), the control section 12 performs the process of step S6, and if not stored (NO at step S5), the control section 12 returns the process to step S4.

As the internal pressure of the air bag 3 increases, the detection face 42 entirely makes contact with the body surface. In the state in which the internal pressure of the air bag 3 is low and the elastic moduli of the air bag 3 and the strain sensor 4 are sufficiently smaller than the elastic modulus of the body surface, the detection face 42 is deformed so as to conform to the body surface. After that, when the internal pressure of the air bag 3 becomes high and the elastic moduli of the air bag 3 and the strain sensor 4 become larger than the elastic modulus of the body surface, the shape of the detection face 42 becomes almost unchanged.

At step S6, the control section 12 determines the timing at which the detection face 42 has not become deformed substantially (the timing at which the deformation of the detection face 42 has been stopped substantially) as described above.

The state in which the deformation of the detection face 42 is stopped substantially is not limited to the state in which the deformation is stopped completely but includes the state in which the deformation of the detection face 42 becomes small to the extent that the influence of the deformation of the detection face 42 on the detection accuracy of the pressure pulse wave can be neglected.

At step S6, more specifically, the control section 12 extracts the strain detection signal group corresponding to the latest detection time (assumed to be detection time tn) stored in the RAM and the strain detection signal group corresponding to the detection time (assumed to be detection time tn−1) preceding the latest detection time stored in the RAM. With respect to these two strain detection signal groups, the control section 12 calculates the difference between the strain detection signals detected by the same strain detection element 41 (the two strain detection signals detected by one strain detection element 41 at the detection time tn and at the detection time tn−1 respectively) and divides the total sum of the calculated differences by the total number of the strain detection elements 41, thereby calculating the average value of the differences.

The fact that the average value of the differences is small means that the change in the shape of the detection face 42 is small. Hence, in the case that the average value of the differences is less than a threshold value, the control section 12 determines that the deformation of the detection face 42 has been stopped substantially at the time tn−1. This threshold value is set to a value in consideration of the difference between the pressing forces at the times when the two strain detection signal groups are detected respectively.

The above-mentioned difference includes the signal difference caused by the difference between the pressure received from the body surface by the pressure force at the detection time tn and the pressure received from the body surface by the pressure force at the detection time tn−1. Consequently, the timing at which the deformation of the detection face 42 has been stopped substantially can be determined accurately by making the threshold value larger than the difference between the signals.

Instead of the above-mentioned difference, the ratio of the two strain detection signals detected at different times by the strain detection element 41 can also be used. Alternatively, in the case that the control section 12 determines that the similarity of such curved shapes as shown in FIG. 5 represented by the respective two strain detection signal groups is not less than the threshold value, it may be possible to determine that the deformation of the detection face 42 has been stopped substantially at the time tn−1.

Each strain detection signal of the two strain detection signal groups for use in the above-mentioned determination may be the DC component of the signal or may be the absolute value of the signal. AC components due to pulsation are scarcely included in the strain detection signals detected before the deformation stop timing. For this reason, the timing at which the deformation of the detection face 42 has been stopped can be determined by either of the DC component and the absolute value.

When the determination at step S6 becomes YES, the control section 12 sets each strain detection signal of the strain detection signal group detected by the strain sensor 4 at the deformation stop timing (the above-mentioned time tn−1), that is, the timing at which the deformation of the detection face 42 has been stopped substantially, as the reference level of the strain detection element 41 from which the strain detection signal is output (At step S7).

At the deformation stop timing, the fluctuations of the strain due to pulsation are not yet large. Hence, each strain detection signal of the strain detection signal group detected by the strain sensor 4 at the deformation stop timing becomes a signal having almost only a DC component.

After the setting of the reference level, with respect to the strain detection signal (hereafter referred to as the first strain detection signal) detected by each strain detection element 41 of the strain sensor 4 after the deformation stop timing, the control section 12 calibrates the first strain detection signal on the basis of the reference level having been set for the strain detection element 41 and stores the calibrated first strain detection signal in the memory 15 in association with the detection time (at step S8).

Figure 6A:
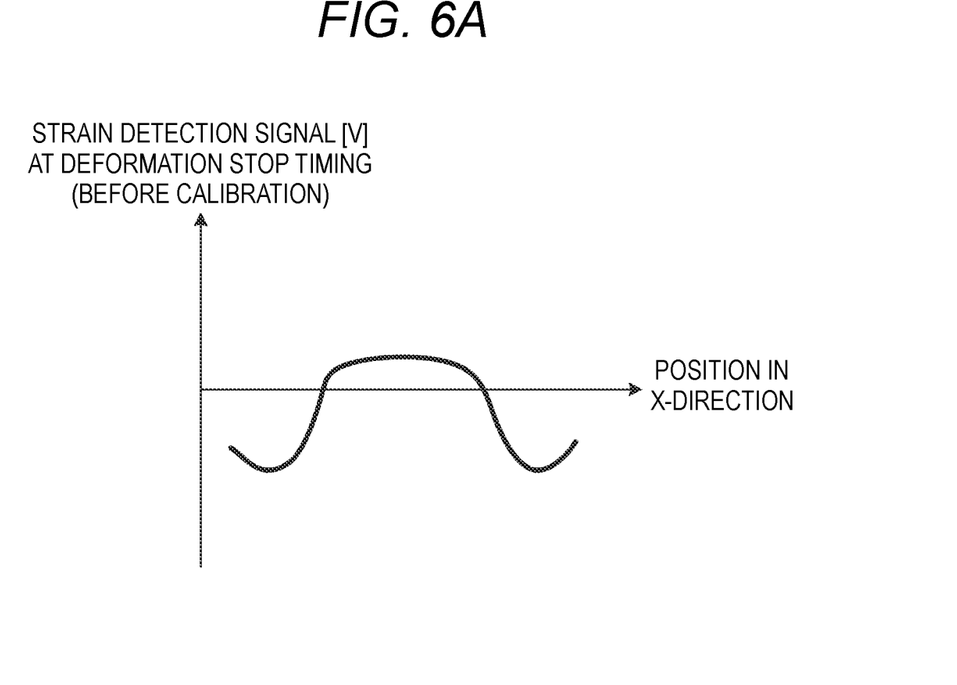
FIG. 6A shows examples of the strain detection signals detected by an arbitrary element row included in the strain sensor 4.
Figure 6B:
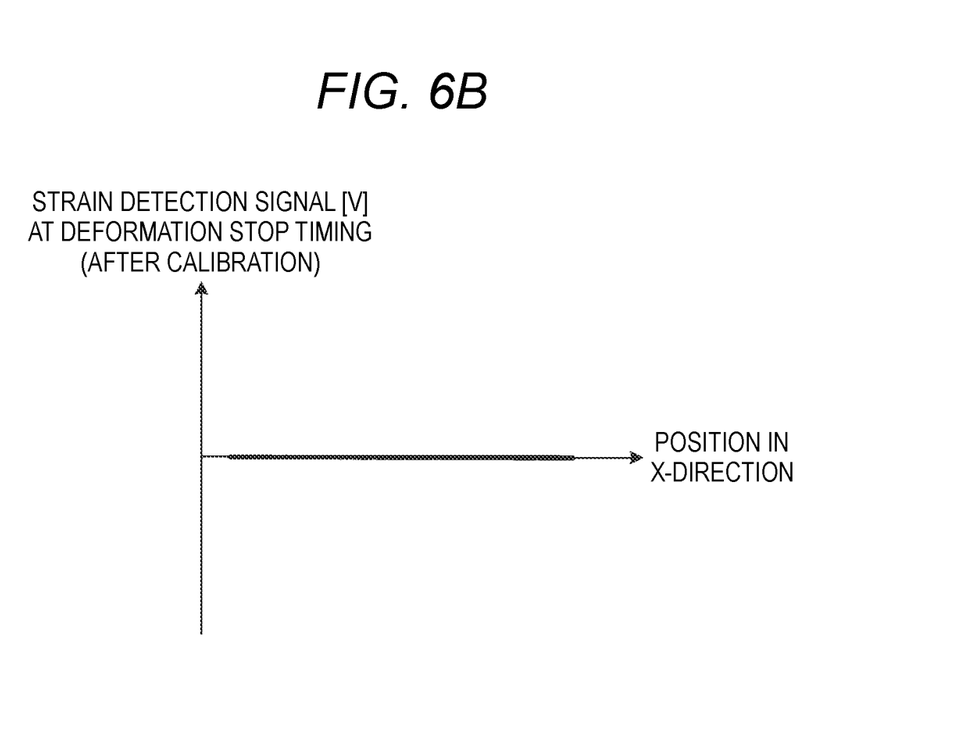
FIG. 6B shows examples of the strain detection signals detected by an arbitrary element row included in the strain sensor 4.

FIGS. 6A and 6B are views showing an example of the strain detection signal detected by an arbitrary element row included in the strain sensor 4. The horizontal axis of the FIG. 6A represents the position of each of the strain detection elements 41 constituting the element row in the X-direction, and the vertical axis of FIGS. 6A and 6B represent the strain detection signal (the value calibrated on the basis of the strain reference value stored in the ROM of the control section 12) detected by each strain detection element 41.

FIG. 6A shows examples of the first strain detection signals detected by an arbitrary element row included in the strain sensor 4 at the above-mentioned deformation stop timing.

FIG. 6B shows the signals obtained after the calibration of the first strain detection signals shown in FIG. 6B. The first strain detection signals obtained at the deformation stop timing are all treated as zero by the processes of step S7 and step S8.

By the process of step S8, the first strain detection signal detected by each strain detection element 41 of the strain sensor 4 after the deformation stop timing and calibrated, the detection time of the calibrated first strain detection signal, and the internal pressure of the air bag 3 at the detection time are going to be stored in the memory 15.

Figure 7:
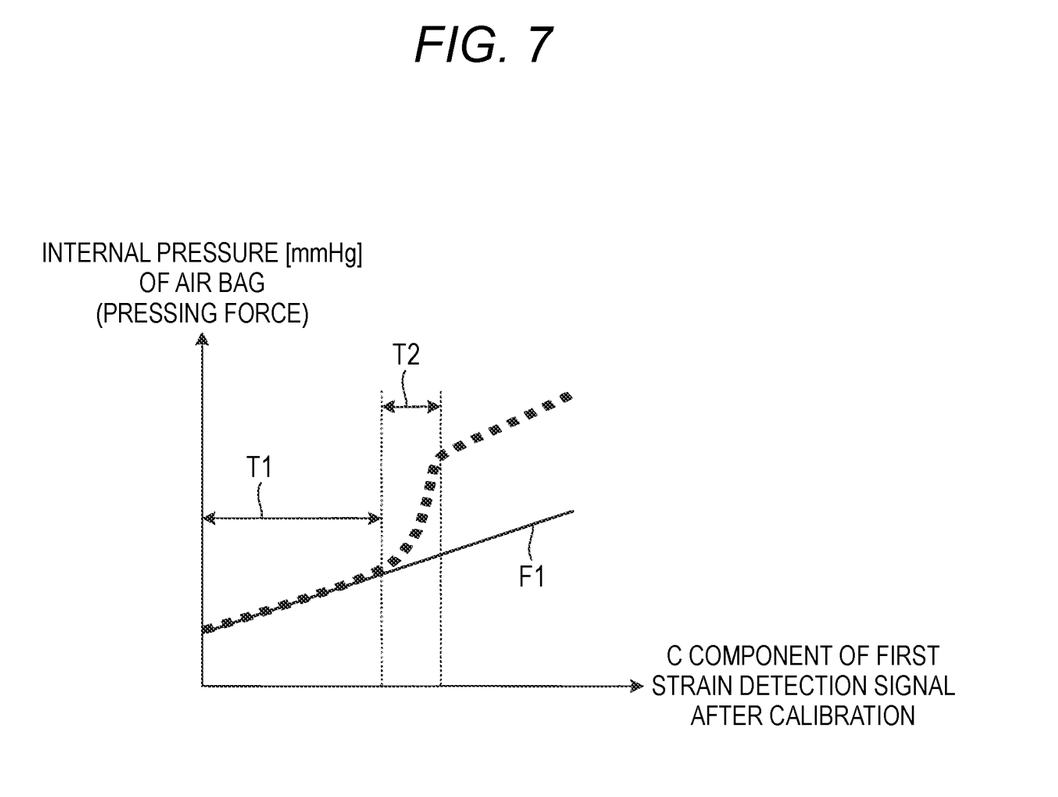
FIG. 7 is a view showing the relationship between the first strain detection signal detected by an arbitrary strain detection element 41 after deformation stop timing and calibrated and the internal pressure of the air bag 3 at the time when the first strain detection signal is detected.

FIG. 7 is a view showing the relationship between the first strain detection signal detected by an arbitrary strain detection element 41 after the deformation stop timing and calibrated and the internal pressure of the air bag 3 at the time when the first strain detection signal is detected.

As described above, the detection face 42 is hardly deformed after the deformation stop timing. Hence, at the early stage (the period T1 in FIG. 7) of the pressing until the radial artery T begins to be flattened by the pressing of the body surface by the strain sensor 4, the DC component of the first strain detection signal detected by each respective strain detection element 41 and calibrated changes linearly as the internal pressure of the air bag 3 increases.

After the period T1 and in the period T2 in which the radial artery T is flattened appropriately and becomes nearly the tonometry state, the change in the DC component of the first strain detection signal with the increase in the internal pressure of the air bag 3 becomes small.

After step S8, on the basis of the DC component of the calibrated first strain detection signal corresponding to each of a plurality of detection times belonging to the period T1 shown in FIG. 7 and the internal pressure of the air bag 3 at each of the plurality of detection times, the control section 12 obtains the coefficients a and b of the linear function $y=ax+b$ representing the relationship between the internal pressure (y) of the air bag 3 and the calibrated first strain detection signal (x) and stores the coefficients in the RAM (at step S9).

The vertical axis data and the horizontal axis data shown in FIG. 7 are stored in the memory 15 for each of all the strain detection elements 41 of the strain sensor 4. On the basis of the stored data of each of all the strain detection elements 41, the control section 12 generates the above-mentioned linear function for each strain detection element 41 and stores the linear function in association with the strain detection element 41.

As an example, the straight line F1 shown in FIG. 7 represents the straight line represented by the linear function $y=ax+b$ generated by the control section 12. The linear function $y=ax+b$ is used as the conversion equation for converting the calibrated first strain detection signal based on the reference level into a pressure signal.

After deriving the linear function at step S9, the control section 12 converts the calibrated first strain detection signal stored in the memory 15 into a pressure signal on the basis of the linear function corresponding to the strain detection element 41 from which the first strain detection signal is output and stores the converted pressure signal in the memory 15 (at step S10).

As a result, the pressure signal corresponding to the first strain detection signal having been detected by each strain detection element 41 of the strain sensor 4 after the deformation stop timing and calibrated, the detection time of the pressure signal, and the internal pressure of the air bag 3 at the detection time are stored in the memory 15. The pressure signal to be stored in the memory 15 is the pressure pulse wave detected by each strain detection element 41.

After step S10, the process is transferred to a pulse wave detection routine.

In the pulse wave detection routine, on the basis of the pressure signal detected in the pressure raising process of the internal pressure of the air bag 3 and stored in the memory 15, the control section 12 selects, for example, the strain detection element 41 in which the AC component of the pressure signal becomes maximum as the optimal element and determines the internal pressure of the air bag 3 at the detection time when the pressure signal having the maximum AC component is detected as the optimal pressing force at which the tonometry state is attained.

After that, the control section 12 holds the internal pressure of the air bag 3 at the optimal pressing force and, in this state, calibrates the respective strain detection signals sequentially detected by the optimal element on the basis of the above-mentioned reference level. On the basis of the above-mentioned linear function generated corresponding to the optimal element, the control section 12 converts the calibrated strain detection signals into pressure signals and stores the converted pressure signals in the memory 15.

On the basis of the pressure signals stored in the memory 15 as described above, the control section 12 calculates blood pressure information including systolic blood pressure and diastolic blood pressure and biological information including heart rate or pulse rate and stores the calculated biological information in the memory 15.

However, the control section 12 is not required to have the biological information calculation function. In this case, a configuration may merely be used in which the pressure signals stored in the memory 15 of the biological information measurement device are transferred to an electronic device, and biological information is calculated and stored in this electronic device.

As described above, the biological information measurement device according to the embodiment determines the timing at which the deformation of the detection face 42 of the strain sensor 4 has been stopped in the pressure raising process and sets the level of the strain detection signal detected by each strain detection element 41 at the timing as the reference level. In other words, the biological information measurement device can detect the strain detection signal with reference to the state in which the strain occurring in each strain detection element 41 has been made almost fixed by the deformation of the strain sensor 4. Consequently, after the above-mentioned timing, the strain detection signal is composed of the strain detected depending on the pressing force and the strain detected depending on pulsation, whereby only the pressure pulse wave can be detected accurately.

Furthermore, the biological information measurement device according to the embodiment generates the conversion equation for converting the strain detection signal into the pressure signal on the basis of the calibrated first strain detection signal. Since the conversion equation is generated by using the biological signal detected from a person to be measured, the reliability of the converted pressure signal can be raised, and the pressure pulse wave can be detected accurately.

It may be possible that the conversion equation for each strain detection element 41 generated on the basis of the first strain detection signals actually measured from numerous persons to be measured and calibrated is stored in the ROM of the control section 12 of the biological information measurement device at the time of manufacturing and that the control section 12 converts the calibrated first strain detection signal into the pressure signal using the conversion equation. With this configuration, the calculation of the conversion equation is not required in the biological information measurement device, whereby the time until the start of biological information measurement can be shortened and the electric power for the biological information measurement device can be saved.

Moreover, with the biological information measurement device according to the embodiment, the conversion equation is generated for each of all the strain detection elements 41 included in the strain sensor 4, and the first strain detection signal detected by an arbitrary strain detection element 41 and calibrated is converted into a pressure signal on the basis of the conversion equation generated for this arbitrary strain detection element 41. Since the conversion equation being different for each strain detection element 41 is applied and the conversion into the pressure signal is performed as described above, the detection accuracy of the pressure pulse wave can be raised.

It may also be possible that the control section 12 selects one (for example, an element located near the center of the detection face 42) of all the strain detection elements 41 included in the strain sensor 4 and generates the conversion equation for converting the strain detection signal into the pressure signal on the basis of the first strain detection signal detected by the selected strain detection element 41 at each of the plurality of detection times belonging to the above-mentioned period T1 and the internal pressure of the air bag 3 at each of the plurality of detection times. With this configuration, the calculation of the conversion equations for all the strain detection elements 41 included in the strain sensor 4 is not required, whereby the time until the start of biological information measurement can be shortened and the electric power for the biological information measurement device can be saved.

In this case, the control section 12 converts the first strain detection signal detected by each strain detection element 41 included in the strain sensor 4 and calibrated into the pressure signal on the basis of the single conversion equation being generated as described above and common to all the strain detection elements 41. With this configuration, the amount of calculations required for the generation of the conversion equations can be reduced, whereby the electric power for the biological information measurement device can be saved.

In the biological information measurement device according to this embodiment, instead of the air bag 3 and the pump 11, it is possible to adopt an air bag having constant internal pressure and being deformable, a pressing mechanism for pressing this air bag against the body surface, and a drive section for driving this pressing mechanism.

With this configuration, the strain sensor 4 is fixed to the air bag having the constant internal pressure and being deformable. The control section 12 controls the drive section to move the pressing mechanism to the body surface. When the pressing mechanism is moved and the strain sensor 4 is pressed against the body surface, the air bag is deformed by the movement of the pressing mechanism for a while, whereby the detection face 42 of the strain sensor 4 is also deformed. When the pressing force becomes high to some extent, the deformation of the air bag is stopped, whereby the deformation of the detection face 42 is also stopped. The control section 12 sets the level of the strain detection signal detected at the timing when the deformation of the detection face 42 has been stopped to the reference level and then performs calibration. With this configuration, the air bag having the constant internal pressure is used as a pressing member having flexibility.

As described above, the following matters are disclosed in the specification.

The disclosed pulse wave detector is equipped with a flexible strain sensor having a plurality of strain detection elements arranged on a substrate; a flexible pressing member for pressing the strain sensor fixed thereto against the body surface of a living body; a drive section for driving the pressing member; a pressing control section for controlling the pressing force of the pressing member for pressing the strain sensor against the body surface by controlling the drive section; a deformation stop timing determination section for determining the deformation stop timing at which the deformation of the detection face of the strain sensor has been stopped on the basis of the strain detection signal detected by each of the plurality of strain detection elements in a pressure raising process in which the pressing force is increased by the pressing control section; a calibration section for setting the level of the strain detection signal detected by each of the plurality of strain detection elements at the deformation stop timing as a reference level and for calibrating the first strain detection signal detected by each of the plurality of strain detection elements after the deformation stop timing on the basis of the reference level; and a pressure generation section for generating a pressure signal from the calibrated first strain detection signal.

In the disclosed pulse wave detector, on the basis of the first strain detection signal detected by the strain detection element at each of a plurality of timings in the period between the deformation stop timing and the time point after a predetermined time has passed from the deformation stop timing in the pressure raising process and calibrated and the pressing force at each of the plurality of timings, the pressure generation section generates a conversion equation for converting the calibrated first strain detection signal into a pressure signal and generates a pressure signal from the calibrated first strain detection signal.

In the disclosed pulse wave detector, with each of the plurality of strain detection elements being used as a target element, on the basis of the first strain detection signal detected by the target element at each of the plurality of timings and calibrated and the pressing force at each of the plurality of timings, the pressure generation section performs a process for generating a conversion equation for converting the calibrated first strain detection signal into a pressure signal for each of the target elements, and generates a pressure signal on the basis of the first strain detection signal detected by an arbitrary one of the strain detection elements and calibrated and the conversion equation generated for the arbitrary strain detection element.

The disclosed pulse wave detector is further equipped with a storage medium for storing the output signal of each of the plurality of strain detection elements as a reference value in the state in which the detection face of the strain sensor is flat, wherein the strain detection signal detected by the strain detection element has been calibrated on the basis of the reference value.

In the disclosed pulse wave detector, the strain sensor includes the plurality of strain detection elements arranged in a two-dimensional form.

The disclosed biological information measurement device is equipped with the pulse wave detector and a biological information calculation section for calculating biological information on the basis of the pressure signal generated by the pressure generation section.

The disclosed pulse wave detection method, using a flexible strain sensor having a plurality of strain detection elements arranged on a substrate and a flexible pressing member for pressing the strain sensor fixed thereto against the body surface of a living body, is provided with the step of increasing the pressing force of the pressing member for pressing the strain sensor against the body surface; the step of determining the deformation stop timing at which the deformation of the detection face of the strain sensor has been stopped on the basis of the strain detection signal detected by each of the plurality of strain detection elements in a pressure raising process in which the pressing force is increased; the step of setting the level of the strain detection signal detected by each of the plurality of strain detection elements at the deformation stop timing as a reference level and calibrating the first strain detection signal detected by each of the plurality of strain detection elements after the deformation stop timing on the basis of the reference level; and the step of generating a pressure signal from the calibrated first strain detection signal.

The disclosed pulse wave detection program, using a flexible strain sensor having a plurality of strain detection elements arranged on the same plane and a flexible pressing member for pressing the strain sensor fixed thereto against the body surface of a living body, makes a computer execute the step of increasing the pressing force of the pressing member for pressing the strain sensor against the body surface; the step of determining the deformation stop timing at which the deformation of the detection face of the strain sensor has been stopped on the basis of the strain detection signal detected by each of the plurality of strain detection elements in a pressure raising process in which the pressing force is increased; the step of setting the level of the strain detection signal detected by each of the plurality of strain detection elements at the deformation stop timing as a reference level and calibrating the first strain detection signal detected by each of the plurality of strain detection elements after the deformation stop timing on the basis of the reference level; and the step of generating a pressure signal from the calibrated first strain detection signal.

The pulse wave detector according to one aspect of the embodiment is equipped with a flexible strain sensor having a plurality of strain detection elements arranged on a substrate; a flexible pressing member for pressing the strain sensor fixed thereto against the body surface of a living body; a drive section for driving the pressing member; a pressing control section for controlling the pressing force of the pressing member for pressing the strain sensor against the body surface by controlling the drive section; a deformation stop timing determination section for determining the deformation stop timing at which the deformation of the detection face of the strain sensor has been stopped on the basis of the strain detection signal detected by each of the plurality of strain detection elements in a pressure raising process in which the pressing force is increased by the pressing control section; a calibration section for setting the level of the strain detection signal detected by each of the plurality of strain detection elements at the deformation stop timing as a reference level and for calibrating the first strain detection signal detected by each of the plurality of strain detection elements after the deformation stop timing on the basis of the reference level; and a pressure generation section for generating a pressure signal from the calibrated first strain detection signal.

The biological information measurement device according to one aspect of the embodiment is equipped with the pulse wave detector and a biological information calculation section for calculating biological information on the basis of the pressure signal generated by the pressure generation section.

The pulse wave detection method according to one aspect of the embodiment, using a flexible strain sensor having a plurality of strain detection elements arranged on a substrate and a flexible pressing member for pressing the strain sensor fixed thereto against the body surface of a living body, is provided with the step of increasing the pressing force of the pressing member for pressing the strain sensor against the body surface; the step of determining the deformation stop timing at which the deformation of the detection face of the strain sensor has been stopped on the basis of the strain detection signal detected by each of the plurality of strain detection elements in a pressure raising process in which the pressing force is increased; the step of setting the level of the strain detection signal detected by each of the plurality of strain detection elements at the deformation stop timing as a reference level and calibrating the first strain detection signal detected by each of the plurality of strain detection elements after the deformation stop timing on the basis of the reference level; and the step of generating a pressure signal from the calibrated first strain detection signal.

The pulse wave detection program according to one aspect of the embodiment, using a flexible strain sensor having a plurality of strain detection elements arranged on the same plane and a flexible pressing member for pressing the strain sensor fixed thereto against the body surface of a living body, makes a computer execute the step of increasing the pressing force of the pressing member for pressing the strain sensor against the body surface; the step of determining the deformation stop timing at which the deformation of the detection face of the strain sensor has been stopped on the basis of the strain detection signal detected by each of the plurality of strain detection elements in a pressure raising process in which the pressing force is increased; the step of setting the level of the strain detection signal detected by each of the plurality of strain detection elements at the deformation stop timing as a reference level and calibrating the first strain detection signal detected by each of the plurality of strain detection elements after the deformation stop timing on the basis of the reference level; and the step of generating a pressure signal from the calibrated first strain detection signal.

The present invention can provide a pulse wave detector capable of accurately detecting a pressure pulse wave in the state in which a flexible sensor is pressed against a body surface, a biological information measurement device, a method for controlling the pulse wave detector, and a program for controlling the pulse wave detector.

The present invention is highly convenient and effective when applied particularly to a sphygmomanometer and the like.

Although the invention has been described with reference to the specific embodiment, the invention is not limited to the embodiment, and various changes can be made without departing from the technical spirit of the disclosed invention.

The invention claimed is:

1. A pulse wave detector comprising:
   a flexible strain sensor having a plurality of strain detection elements arranged on a substrate;
   a flexible pressing member configured to press the strain sensor fixed thereto against a body surface of a living body;
   a drive section configured to drive the pressing member; and
   a controller configured to
      control a pressing force of the pressing member for pressing the strain sensor against the body surface by controlling the drive section,
      determine a deformation stop timing at which deformation of a detection face of the strain sensor has been stopped based on a strain detection signal detected by each of the plurality of strain detection elements in a pressure raising process in which the pressing force is increased by the controller,
      set a level of the strain detection signal detected by each of the plurality of strain detection elements at the deformation stop timing as a reference level,
      calibrate a first strain detection signal detected by each of the plurality of strain detection elements after the deformation stop timing based on the reference level, and
      generate a pressure signal from the calibrated first strain detection signal.

2. The pulse wave detector according to claim 1, wherein based on the first strain detection signal that has been detected by at least one of the strain detection elements at each of a plurality of timings in a period between the deformation stop timing and a time point after a predetermined time has passed from the deformation stop timing in the pressure raising process and has been calibrated, and the pressing force at each of the plurality of timings, the controller generates a conversion equation that converts the calibrated first strain detection signal into the pressure signal and generates the pressure signal from the calibrated first strain detection signal.

3. The pulse wave detector according to claim 2, wherein with each of the plurality of strain detection elements being used as a target element, based on the first strain detection signal that has been detected by the target element at each of the plurality of timings and has been calibrated, and the pressing force at each of the plurality of timings, the controller performs a process for generating the conversion equation that converts the calibrated first strain detection signal into the pressure signal for each of the target elements, and generates the pressure signal based on the first strain detection signal that has been detected by an arbitrary one of the plurality of strain detection elements and has been calibrated, and the conversion equation generated for the arbitrary strain detection element.

4. The pulse wave detector according to claim 1, further comprising a storage medium for storing an output signal of each of the plurality of strain detection elements as a reference value in a state in which the detection face of the strain sensor is flat, wherein
   the strain detection signals detected by the strain detection elements are respectively calibrated based on the reference values.

5. The pulse wave detector according to claim 1, wherein the strain sensor includes the plurality of strain detection elements arranged in a two-dimensional form.

6. A biological information measurement device comprising:
   a pulse wave detector, wherein
   the pulse wave detector comprises:
      a flexible strain sensor having a plurality of strain detection elements arranged on a substrate;
      a flexible pressing member configured to press the strain sensor fixed thereto against a body surface of a living body;
      a drive section configured to drive the pressing member; and
      a controller configured to
         control a pressing force of the pressing member for pressing the strain sensor against the body surface by controlling the drive section;
         determine a deformation stop timing at which deformation of a detection face of the strain sensor has been stopped based on a strain detection signal detected by each of the plurality of strain detection elements in a pressure raising process in which the pressing force is increased by the controller;
         set a level of the strain detection signal detected by each of the plurality of strain detection elements at the deformation stop timing as a reference level,
         calibrate a first strain detection signal detected by each of the plurality of strain detection elements after the deformation stop timing based on the reference level,
         generate a pressure signal from the calibrated first strain detection signal, and
         calculate biological information based on the pressure signal.

7. A pulse wave detection method, comprising:
   increasing a pressing force of a pressing member configured to press a flexible strain sensor fixed thereto against a body surface, the strain sensor having a plurality of strain detection elements arranged on a substrate;
   determining a deformation stop timing at which deformation of a detection face of the strain sensor has been stopped based on the strain detection signal detected by each of the plurality of strain detection elements in a pressure raising process in which the pressing force is increased;
   setting a level of the strain detection signal detected by each of the plurality of strain detection elements at the deformation stop timing as a reference level;
   calibrating a first strain detection signal detected by each of the plurality of strain detection elements after the deformation stop timing based on the reference level; and
   generating a pressure signal from the calibrated first strain detection signal.

8. A computer-readable non-transitory storage medium that stores a program for causing a computer to execute a process, the process comprising:
   increasing a pressing force of a pressing member configured to press a flexible strain sensor fixed thereto against a body surface, the strain sensor having a plurality of strain detection elements arranged on a substrate;
   determining a deformation stop timing at which deformation of a detection face of the strain sensor has been stopped based on the strain detection signal detected by each of the plurality of strain detection elements in a pressure raising process in which the pressing force is increased;

setting a level of the strain detection signal detected by each of the plurality of strain detection elements at the deformation stop timing as a reference level;

calibrating a first strain detection signal detected by each of the plurality of strain detection elements after the deformation stop timing based on the reference level; and generating a pressure signal from the calibrated first strain detection signal.

* * * * *